(12) United States Patent
LaCroix

(10) Patent No.: US 10,368,594 B1
(45) Date of Patent: Aug. 6, 2019

(54) STABILIZED SUPPORT DEVICE FOR A LIMB GUARD

(71) Applicant: Normand P. LaCroix, Milpitas, CA (US)

(72) Inventor: Normand P. LaCroix, Milpitas, CA (US)

( * ) Notice: Subject to any disclaimer, the term of this patent is extended or adjusted under 35 U.S.C. 154(b) by 0 days.

(21) Appl. No.: 15/938,989

(22) Filed: Mar. 28, 2018

(51) Int. Cl.
| | |
|---|---|
| *A41D 13/05* | (2006.01) |
| *A41D 13/06* | (2006.01) |
| *A41D 13/08* | (2006.01) |
| *A41D 27/10* | (2006.01) |
| *A61F 5/01* | (2006.01) |

(52) U.S. Cl.
CPC ....... *A41D 13/0568* (2013.01); *A41D 13/065* (2013.01); *A41D 13/08* (2013.01); *A41D 27/10* (2013.01); *A61F 5/0109* (2013.01)

(58) Field of Classification Search
CPC .. A41D 13/0568; A41D 13/08; A41D 13/065; A41D 13/06; A41D 27/10; A61F 5/0109
USPC ................ 2/20, 24, 44, 45, 22, 16
See application file for complete search history.

(56) References Cited

U.S. PATENT DOCUMENTS

| | | | | |
|---|---|---|---|---|
| 537,607 A | * | 4/1895 | Green ................ | A01K 13/007 54/82 |
| 563,468 A | * | 7/1896 | Fergusson ............ | A41D 13/065 2/24 |
| 696,764 A | * | 4/1902 | Shibe ................ | A63B 71/1225 2/22 |
| 770,619 A | * | 9/1904 | Waller ................ | A47J 17/02 2/16 |
| 1,136,307 A | * | 4/1915 | Bourdon ............ | A41D 13/018 2/16 |
| 1,945,226 A | * | 1/1934 | Lutsche ................ | A01K 13/007 2/24 |
| 2,607,920 A | * | 8/1952 | Lawrence .......... | A41D 13/0568 2/231 |
| 3,463,147 A | * | 8/1969 | Stubbs ................ | A61F 13/062 2/24 |
| 4,177,806 A | * | 12/1979 | Griffin ................ | A61F 13/062 128/892 |

(Continued)

FOREIGN PATENT DOCUMENTS

CN           202842435           4/2013

OTHER PUBLICATIONS

Web site page for Bauer Performance Shin Guard (original publication date unknown) from Internet address: https://www.hockeygiant.com/product/Street_Hockey_Shin_Guards/itm/17044-41/?mtx_id=0.

(Continued)

*Primary Examiner* — Shaun R Hurley
*Assistant Examiner* — Bao-Thieu L Nguyen
(74) *Attorney, Agent, or Firm* — GSS Law Group; Gregory S. Smith; Phillip M. Wagner

(57) ABSTRACT

A device for coupling a limb guard to a human limb includes a support sleeve configured to wrap around the limb. The support sleeve includes a friction pad configured to cushion the limb and oppose translational and rotational displacement of the device relative to the limb. The support sleeve provides a stable attachment surface for a joint guard and/or limb guard and may be worn without discomfort for extended periods, remaining stationary relative to the limb while a person wearing the device moves about.

12 Claims, 10 Drawing Sheets

(56) References Cited

U.S. PATENT DOCUMENTS

| | | | | |
|---|---|---|---|---|
| 4,692,946 A * | 9/1987 | Jurga | A63B 71/1225 | 2/22 |
| 4,772,071 A | 9/1988 | Richards | | |
| 4,876,745 A | 10/1989 | Richards | | |
| 4,999,847 A * | 3/1991 | Barcelo | A63B 71/1225 | 2/22 |
| 5,024,216 A * | 6/1991 | Shiono | A61F 5/0123 | 2/24 |
| 5,375,262 A * | 12/1994 | Carter | A41D 13/0543 | 2/22 |
| 5,455,969 A * | 10/1995 | Pratson | A41D 13/0568 | 2/24 |
| 5,456,658 A * | 10/1995 | Duback | A41D 13/0153 | 2/22 |
| 5,537,689 A * | 7/1996 | Dancyger | A41D 13/0568 | 2/24 |
| 5,570,470 A * | 11/1996 | Miller | A41D 13/06 | 2/22 |
| 5,572,737 A * | 11/1996 | Valice | A41D 1/067 | 2/22 |
| 5,634,211 A * | 6/1997 | Chen | A63B 71/1225 | 2/22 |
| 5,784,715 A * | 7/1998 | Buchanan | A63B 71/1225 | 2/22 |
| 5,920,902 A | 7/1999 | Crampton | | |
| 5,926,843 A * | 7/1999 | Winchester | A61D 9/00 | 119/850 |
| 5,946,737 A * | 9/1999 | Fleege | A41D 13/06 | 2/16 |
| 6,058,505 A | 5/2000 | Bettencourt | | |
| 6,098,208 A * | 8/2000 | Cordon | A63B 71/08 | 2/16 |
| 6,253,376 B1 | 7/2001 | Ritter | | |
| 6,317,888 B1 | 11/2001 | McFarlane | | |
| 6,347,403 B1 | 2/2002 | Wilcox | | |
| 6,553,572 B2 * | 4/2003 | Fiorini | A41D 13/065 | 2/22 |
| 6,553,573 B1 | 4/2003 | Brown | | |
| 6,585,673 B1 * | 7/2003 | Bass | A61F 7/02 | 128/845 |
| 6,623,835 B2 * | 9/2003 | Chang | A41D 13/0568 | 2/24 |
| 6,832,390 B1 | 12/2004 | Kleinert | | |
| D501,690 S * | 2/2005 | Chen | D29/120.1 | |
| 6,912,729 B2 * | 7/2005 | Nishimoto | A63B 71/1225 | 2/22 |
| 6,964,062 B1 * | 11/2005 | Chen | A41D 13/065 | 2/22 |
| 6,988,281 B1 | 1/2006 | Jerome | | |
| 7,096,507 B1 * | 8/2006 | Bolden | A41D 13/05 | 2/22 |
| 7,188,370 B2 * | 3/2007 | Bevier | A63B 71/1225 | 2/22 |
| 7,219,372 B2 | 5/2007 | Frieler | | |
| 7,380,283 B1 | 6/2008 | Dumont | | |
| 7,451,493 B2 * | 11/2008 | Godshaw | A41D 13/0568 | 2/24 |
| 7,712,150 B2 | 5/2010 | Pardillo | | |
| 7,725,951 B2 | 6/2010 | Rampersad | | |
| 7,749,183 B2 * | 7/2010 | Ingimundarson | A61F 5/0123 | 2/24 |
| 7,797,759 B2 | 9/2010 | Cunningham | | |
| 7,832,017 B2 * | 11/2010 | Nascimento | A63B 71/1225 | 2/22 |
| 7,845,017 B2 * | 12/2010 | Godshaw | A41D 13/0568 | 2/24 |
| 7,900,271 B2 * | 3/2011 | Sonner | A41D 13/065 | 2/2.5 |
| 7,937,768 B2 | 5/2011 | Behrend | | |
| 7,937,769 B2 | 5/2011 | Richards | | |
| 7,979,922 B2 * | 7/2011 | Ronco | A41D 13/0153 | 2/24 |
| 8,256,021 B2 * | 9/2012 | Nascimento | A63B 71/1225 | 2/22 |
| 8,752,214 B1 | 6/2014 | Maldonado | | |
| 8,931,112 B1 * | 1/2015 | Furst | A41D 13/065 | 2/22 |
| 8,959,668 B1 * | 2/2015 | Ganes | A42B 3/08 | 2/410 |
| 9,144,253 B1 * | 9/2015 | Munter | A41D 13/065 | |
| 2005/0120456 A1 | 6/2005 | Cunningham | | |
| 2006/0041986 A1 * | 3/2006 | Godshaw | A41D 13/0568 | 2/24 |
| 2006/0107433 A1 * | 5/2006 | Olson | A61F 5/0104 | 2/22 |
| 2007/0150993 A1 | 7/2007 | Oh | | |
| 2008/0115248 A1 | 5/2008 | Meadows | | |
| 2008/0222767 A1 | 9/2008 | Williams | | |
| 2008/0300522 A1 * | 12/2008 | Chen | A61F 5/028 | 602/19 |
| 2009/0113592 A1 * | 5/2009 | Iwata | A41D 19/01523 | 2/19 |
| 2009/0210990 A1 * | 8/2009 | Taylor | A41D 13/0543 | 2/22 |
| 2010/0205711 A1 | 8/2010 | Schantz | | |
| 2011/0094001 A1 | 4/2011 | Maldonado | | |
| 2012/0066811 A1 * | 3/2012 | Noble | A41D 13/01 | 2/24 |
| 2012/0180183 A1 * | 7/2012 | Mechling | A41D 13/0543 | 2/22 |
| 2012/0260392 A1 * | 10/2012 | Votel | A41D 13/065 | 2/24 |
| 2013/0007938 A1 * | 1/2013 | LoCicero | A41D 13/06 | 2/24 |
| 2013/0061365 A1 | 3/2013 | Arceo | | |
| 2013/0291275 A1 * | 11/2013 | Radefeldt | A41D 13/001 | 2/24 |
| 2014/0230116 A1 * | 8/2014 | Weber | A41D 13/0568 | 2/22 |
| 2014/0283275 A1 * | 9/2014 | Pratson | A41D 13/065 | 2/24 |
| 2015/0047090 A1 * | 2/2015 | Cook | A41D 13/0543 | 2/22 |
| 2015/0128325 A1 * | 5/2015 | Vaughn | A63B 71/1225 | 2/22 |
| 2015/0250236 A1 * | 9/2015 | Garcia | A41D 13/0543 | 2/22 |
| 2015/0296899 A1 * | 10/2015 | Wyner | A41D 13/0543 | 2/16 |
| 2015/0360116 A1 * | 12/2015 | Contant | A63B 71/1225 | 2/22 |
| 2016/0030251 A1 * | 2/2016 | Schuren | A61F 5/0109 | 602/75 |
| 2016/0044978 A1 * | 2/2016 | Callaway | A41D 17/005 | 2/22 |
| 2016/0095362 A1 * | 4/2016 | Alomar, Jr. | A41D 13/065 | 2/22 |
| 2016/0095363 A1 * | 4/2016 | Alomar, Jr. | A41D 13/065 | 2/24 |
| 2017/0055603 A1 * | 3/2017 | Guidetti | A41D 13/0543 | |

OTHER PUBLICATIONS

Web site page for Shock Doctor calf wrap (original publication date unknown) from Internet address: https://www.shockdoctor.com/calf-shin-wrap.

Pollard, J.P. et al., "Forces and Moments on the Knee During Kneeling and Squatting", J Appl Biomech, Aug. 2011; 27(3), 233-241.

* cited by examiner

Section A-A

Alternative Section A-A

Alternative Section A-A

Alternative Section A-A

Alternative Section A-A

Alternative Section A-A

STABILIZED SUPPORT DEVICE FOR A LIMB GUARD

FIELD OF THE INVENTION

The present invention relates generally to an attachment device for a padded guard for protecting a person's limb from injury, and more particularly to devices for attaching a knee pad, elbow pad, shin guard, foot guard, or arm guard to a person's limb.

BACKGROUND

A person's limbs and joints are susceptible to pain and injury from impacts, abrasion, and sustained contact pressure. Various protective devices may be worn to relieve discomfort and reduce injury by absorbing impact energy and distributing applied loads over an extended contact area on a person's body. Protective devices may be worn to shield body parts from blunt force trauma, cuts, and abrasions. For example, a person may wear knee pads to reduce discomfort resulting from kneeling on a hard surface. Elbow pads may be worn to prevent joint injuries that may result from a fall or collision with a hard object. Shin guards and forearm guards may be used to protect limbs and may be combined with padded guards for joints in limbs or may be worn without guards or pads for joints. Foot guards or shoe covers may be worn to protect a foot from being injured by a dropped object.

Knee pads, elbow pads, and other protective devices may include one or more pairs of straps, ties, elastic bands, or other attachment means disposed to hold a pad made of a resilient, compressible material over a joint or limb. The straps or other attachment means may be placed in direct contact with a person's skin or may be worn over the person's clothing. A protective device may be shaped to conform to the curved surfaces of the joint or limb the device is intended to cover or may be flexible enough to conform to the limb when the straps are tightened. The device may be covered by a shell or cap made from a strong material such as a high-density polymer, an epoxy-fiber composite, metal, synthetic rubber, natural rubber, polysiloxane, fabric, or combinations of these materials. The shell or cap may be positioned to deflect or distribute energy from loads applied to a joint or limb and may be strong enough to withstand impacts and durable enough to withstand abrasion.

A problem common to many knee pads, elbow pads, shin guards, and forearm guards is the difficulty in keeping the device in a preferred position over a joint and/or limb while the person wearing the device moves about. Flexing a limb joint may cause the protective device to move away from the area the device is intended to protect due to the expansion and contraction of muscles, tendons, and other tissues. The device may slip away from its preferred position when an external force is applied to the device, for example when a person wearing knee pads moves about in a kneeled position. The protective device may slide or rotate away from the joint or protected part of a limb, leaving the protected area exposed to impact and contact pressure and possibly exposing the person wearing the pad to pain or injury.

Some devices attempt to maintain a stable position on a limb by gripping the limb with more than one pair of straps. A first pair of straps may wrap around a limb on one side of a joint to be covered by the device and a second pair may wrap around the limb on the opposite side of the joint, with the protective device extending across the joint between the pairs of straps. Some devices use more than one pair of straps on a same side of a joint to hold the device in a preferred position. Whether a pad or guard has one pair of straps or more than one pair, the repeated change in the outer shape of a limb from flexing and relaxing muscles may cause the straps to loosen or may cause the protective device to creep away from its preferred position over a joint while a person moves about. A person experiencing these problems may attempt to tighten the straps to hold the pad in a preferred position for protection and comfort. However, tightening the straps may impair the movements of muscles and tendons near a joint, reduce blood circulation, or cause bruising or chafing.

Some protective devices attempt to avoid positioning problems and discomfort caused by straps by inserting the device into a pocket in a garment or by clamping to a structure such as a strap, grommet, or ridge on a garment. Such protective devices may not be effective unless one also wears the associated modified garment. In some cases, parts of the modified garment interposed between the protective device and an external object may be damaged by abrasion, cutting, or impact. The protective device may be easily shifted away from a preferred position over a joint or limb by movements of the garment, possibly exposing the person wearing the garment to discomfort or injury. The cost of the modified garment may add to the cost of purchasing and using the protective device.

SUMMARY

An example of an apparatus embodiment includes a support sleeve configured to wrap around a limb and remain in a fixed position on the limb. A friction pad is positioned on a back surface of the support sleeve to cushion the limb and oppose linear and rotational displacement of the support sleeve relative to the limb. A friction pad may alternatively be formed as an integral part of the back surface of the support sleeve. The support sleeve is further configured for attachment to the limb without any straps on the sleeve holding to the limb on both the distal and proximal sides of a joint in the limb.

The support sleeve may include a first collar attached to the support sleeve, the first collar extending transversely across the support sleeve near a first edge. The first collar may be positioned on a front surface of the support sleeve. The support sleeve may further include a second collar attached to the support sleeve, the second collar extending transversely across the support sleeve near a second edge opposite the first edge. The friction pad may extend from a proximal edge of a back side of the support sleeve to an opposite distal edge.

Some embodiments include a joint guard having a pair of straps configured to wrap around the support sleeve with the support sleeve interposed between the straps and the limb. The joint guard may include a detachable cap.

DESCRIPTION

Figure 1:
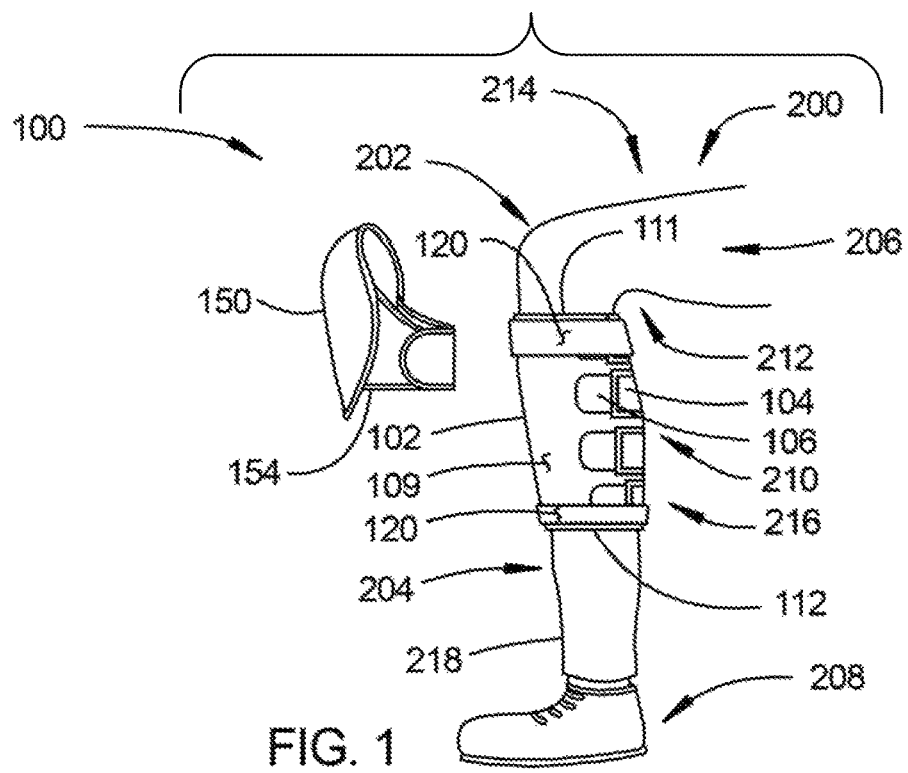
FIG. 1 shows a side view of an example of an apparatus embodiment for holding a joint guard and/or limb guard in a fixed position on a human limb.

An example apparatus embodiment provides a support sleeve configured to remain in a fixed position on a person's limb as the person flexes and straightens the limb while moving about. The support sleeve provides a stable, fixed mounting location for a limb guard or other device connected directly to the support sleeve or alternately held to the support sleeve with an article of clothing intervening between the limb guard and support sleeve. The support sleeve includes one, and in some embodiments, two transverse low-stretch collars disposed to prevent expansion and contraction of the support sleeve at the position of the collar in response to externally applied forces and movements of muscles, tendons, ligaments, or other anatomical structures in the person's limb. A longitudinal pad on the sleeve opposes longitudinal and rotational displacement of the sleeve relative to the limb. The longitudinal pad may also be referred to herein as a friction pad. The collars and friction pad work together to effectively oppose movement of the support sleeve away from an initial position on the limb, thereby providing a stable support for a joint guard and/or limb guard worn over the support sleeve.

The support sleeve may be attached to the limb by one or more pairs of flexible straps. The straps are positioned on the support sleeve in such a manner that all of the straps wrap around a limb on the same side of a joint in the limb. A support sleeve may be configured to have all straps on the sleeve worn on a distal side of a limb joint or may alternatively be configured to have all straps on the sleeve worn on a proximal side of a limb joint. For example, a support sleeve may be worn with all straps wrapped around a leg between the knee joint and foot. Similarly, a support sleeve sized to fit on an arm may be worn between the elbow joint and wrist, with none of the straps wrapped around the arm between the elbow and shoulder. More generally, the support sleeve is configured for attachment to a limb without a strap on the sleeve holding to the limb on a distal side of a limb joint and another strap on the sleeve holding to the limb on a proximal side of the same limb joint.

The collar and friction pad on the support sleeve preferably have lower stretch than other parts of the support sleeve even when moving muscles and tendons near a joint exert force against the support sleeve. The collar and friction pad cooperate to prevent the support sleeve from being displaced from a preferred fixed position by movements of parts of the limb or external forces applied to a protective device coupled to the support sleeve.

Some embodiments include a limb guard with the support sleeve. A limb guard in accord with an embodiment protects a joint, a length of a limb, or both a joint and a segment of a limb from injury or discomfort caused by, for example, impact, chafing from repeated movements, contact with hard, abrasive, or sharp objects, and sustained localized pressure. Examples of a limb guard include, but are not limited to, a knee pad, an elbow pad, a shin guard, a forearm guard, a foot guard, a protective shoe cover, and a hand guard, and combinations of these guards.

The disclosed apparatus embodiments are comfortable when worn for extended periods and provide a fixed position for attachment of limb guards and other devices, thereby avoiding the repeated adjustment of straps, ties, or buckles associated with previously known protective devices. The disclosed apparatus is effective as a stable, fixed support for a limb guard when worn directly against bare skin, when worn over an article of clothing, or when worn with the support sleeve against bare skin and an article of clothing intervening between the support sleeve and a limb guard coupled to the support sleeve.

The examples to follow use a human leg as an example of a limb. Alternative apparatus embodiments may be configured for use on a human arm. A substitution of an arm may be made for the leg in the figures, with the support sleeve attached to the forearm between the elbow joint and hand, and with the limb guard positioned over the elbow joint.

Unless otherwise noted, directional references are given with respect to the limb to which the support sleeve is attached: longitudinal is parallel to the longest dimension of a limb segment; transverse is across a width of a limb segment, perpendicular to the longitudinal direction; and rotational is about an axis parallel to the longitudinal direction. Proximal refers to a direction along a limb toward to a person's torso and distal refers to a direction along a limb away from a person's torso. Proximal and distal may be used for describing a direction on a limb or a direction on an article to be worn on a limb.

An example of an apparatus embodiment 100 is shown in FIG. 1. An example of a support sleeve 102 wraps around a leg 200 below the kneecap 202 and hollow of the knee joint 212 on the back of the leg, extending downward along the shin 204. In the example of FIG. 1, the support sleeve 102 is worn over a garment 218, with the garment intervening between the support sleeve and the person's leg. The support sleeve 102 may alternatively be worn under the garment 218, in contact with the person's skin, with the garment intervening between the sleeve 102 and the limb guard 150 or may alternatively wear both the support sleeve and limb guard underneath a garment, or over a limb with no part of a garment in contact with either the sleeve or limb guard. In the example of FIG. 1, the limb guard 150 is shaped to cover and protect a person's knee and kneecap 202.

The support sleeve 102 may be worn with the proximal edge 111 of the support sleeve about one inch from the distal side 216 of the knee joint 212 to avoid restricting movements of tendons and muscles associated with joint motion and/or to reduce discomfort from pinching by the straps 104 near the knee joint 212. After being wrapped around a limb, the support sleeve is secured by straps 104 held by strap connectors 106. The straps may be made from an elastic material and are preferably set tight enough to prevent the support sleeve from slipping along or around the limb, but not so tight as to cause discomfort. In the example of FIG. 1, all of the straps 104 on the support sleeve 102 wrap around the limb 200 on a distal side 216 of the limb joint 212, with none of the straps 104 on the proximal side 214 of the joint.

The example of a support sleeve in FIG. 1 is preferably long enough to extend beyond the proximal and distal ends of a bulge 210 formed on the back of the leg by the contracted calf muscle, with the proximal transverse edge 111 positioned between the bulge and the knee joint 212 and the distal transverse edge 112 between the bulge and the distal end of the limb. A support sleeve for an arm is preferably long enough to extend over the bulge formed by the contracted muscles of the forearm, from the proximal end of the bulge near the elbow to the distal end of the bulge near the wrist. The support sleeve is preferably made from an elastic material that stretches and contracts with the formation and relaxation of the bulge in the limb caused by movements of the underlying muscle. For example, a support sleeve embodiment 102 may be made from an elastic material including, but not limited to, lycra, elastic polyurethane, elastane, spandex, neoprene, and synthetic rubber, individually or in any combination or subcombination.

Figure 2:
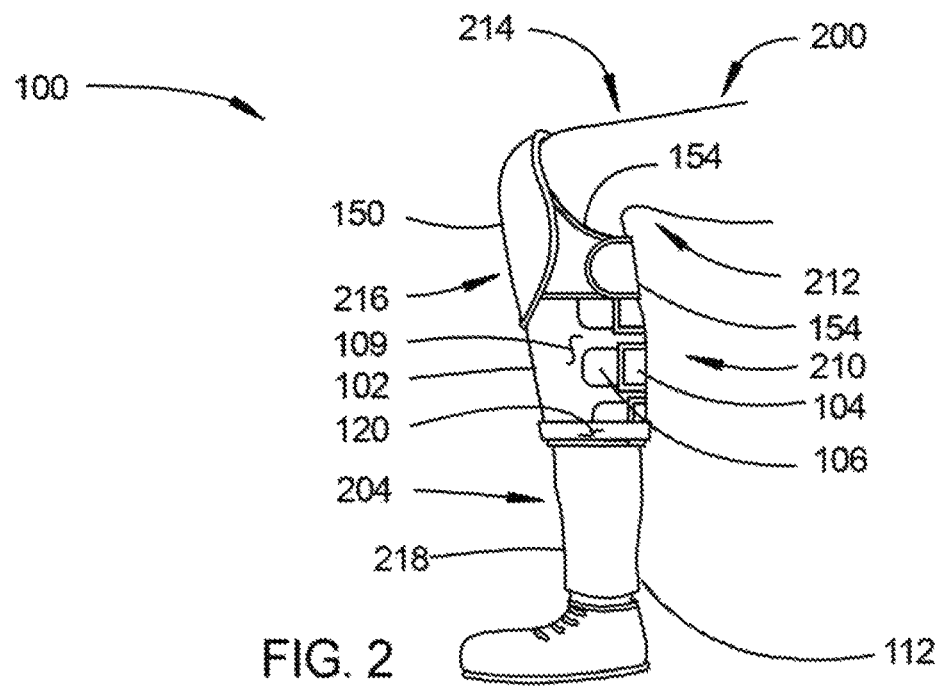
FIG. 2 shows a side view of the example of the apparatus from FIG. 1 with the joint guard worn over a support sleeve.

As suggested in FIG. 1 and FIG. 2, a sleeve embodiment may have a preferred orientation on a limb, with the sleeve having a proximal transverse edge 111 closest to a joint in a limb and a distal transverse edge 112 opposite the proximal edge. Collars 120 for each transverse edge (111, 112) may optionally have different lengths from one another. The sleeve may have a shape that gives it a preferred orientation on a limb. Wearing the sleeve in another orientation, for example upside-down compared to the example of FIGS. 1 and 2, may not be possible or may at least be uncomfortable. An alternative embodiment of a sleeve 102 may be configured to be worn with either transverse edge (111, 112) as the proximal edge.

As suggested in FIGS. 1 and 2, the support sleeve 102 is preferably wrapped around a limb with the low-stretch collar 120 along the proximal edge 111 positioned between the proximal end of the bulge 210 of the contracted limb muscle and the distal side 216 of the knee joint 212. A second optional collar 120 along the distal transverse edge 112 of the support sleeve 102 may be positioned beyond the distal end of the muscle bulge 210. The straps 154 of the limb guard 150 are preferably wrapped over the support sleeve 102. Interposing the support sleeve between the limb guard and the limb provides a stable, comfortable support for the limb guard without uncomfortable pressure or pinching of the limb.

Figure 3:
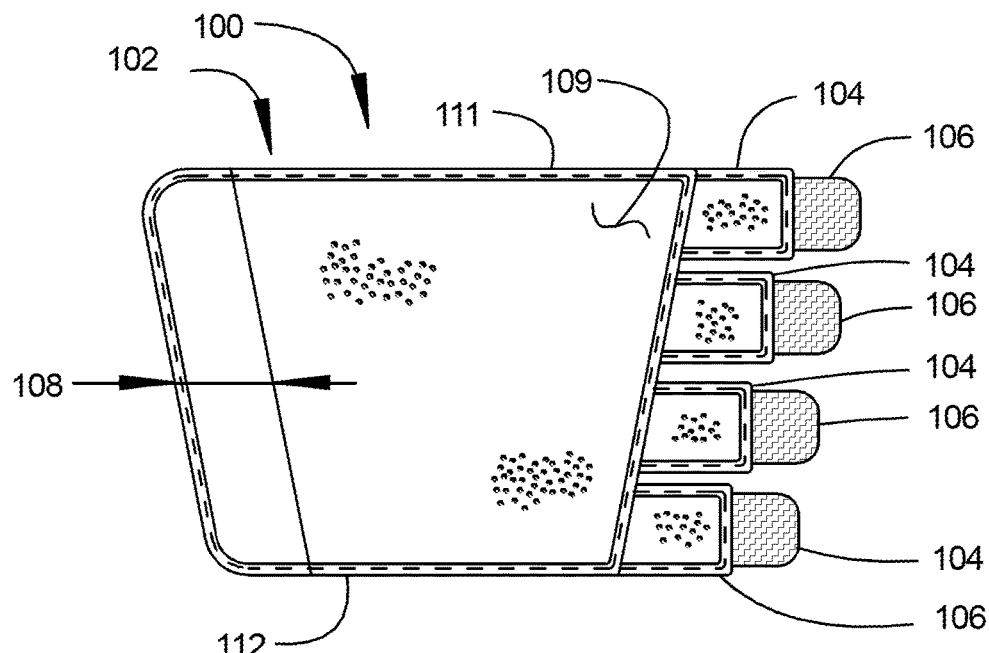
FIG. 3 shows a view toward a front surface of an example of a support sleeve.
Figure 4:
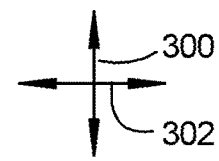
FIG. 4 shows a view toward a back surface of the support sleeve of FIG. 3.
Figure 4:
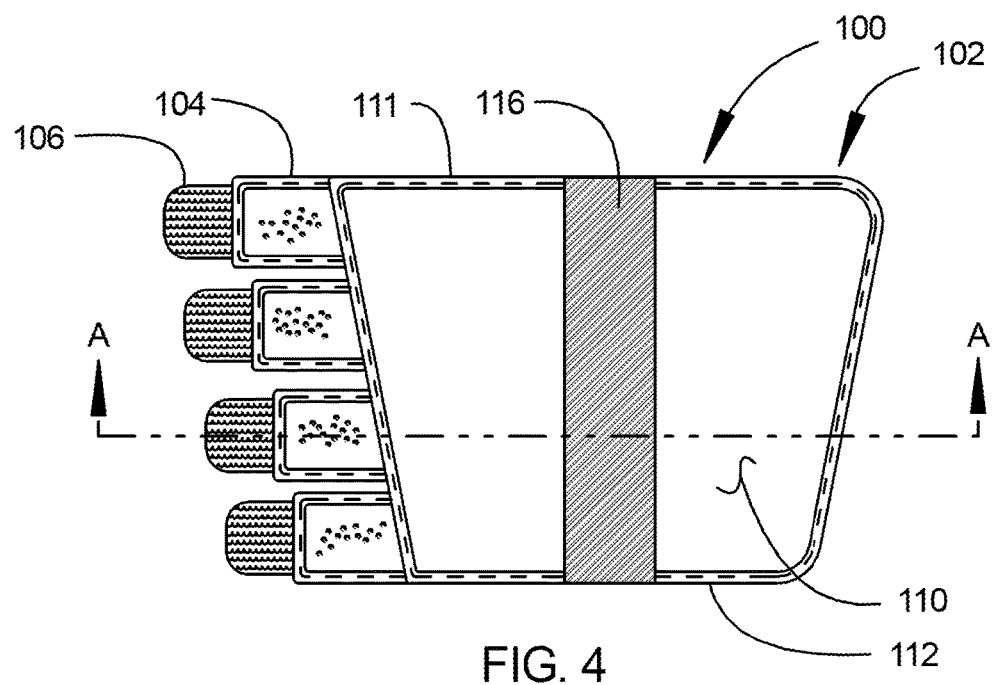

Some details of an example of a support sleeve 102 are shown in a view toward the front surface 109 of the support sleeve in FIG. 3 and a view toward the back surface 110 in FIG. 4. The back surface 110 is the side of the support sleeve 102 closest to the limb while the sleeve is being worn. An elastic strap 104 with a strap connector 106 extends in a transverse direction 302 outward from an edge of the support sleeve 102. More than one elastic strap 104, each with its own strap connector 106, may be included on the support sleeve. The straps 104 are positioned to wrap around a limb and join to one or more complementary strap connectors 108 along an edge of the support sleeve opposite the straps 104. A separate complementary connector 108 may optionally be provided for each strap connector 106. In an alternative embodiment, some or all of the front surface 109 of the support sleeve 102 may be formed from a material comprising the complementary connector 108. Examples of the strap connector 106 and complementary connector 108 include, but are not limited to, hook-and-loop fastener material, a metal and/or plastic hook engaging a corresponding loop or grommet, snaps, magnets, and buttons and buttonholes. Hook-and-loop fastener material may be referred to as thistle cloth. In some embodiments, a strap 104 along one side of the support sleeve may join to another strap extending outward from an opposite side of the support sleeve.

At least one friction pad 116 extends along the back surface 110 of the support sleeve 102 in a longitudinal direction 300. An embodiment 100 may optionally have more than one friction pad 116. In some embodiments, the friction pad 116 extends from the proximal edge 111 to the distal edge 112 of the support sleeve 102, although alternative embodiments may use friction pads of other lengths. The friction pad is preferably made from a material which effectively opposes slipping when pressed against any one or more of skin, another friction pad, and fabric. A material for a friction pad preferably has a high coefficient of friction compared to coefficients of friction for natural and synthetic materials commonly used for clothing. Examples of materials for a friction pad (116, 118) include, but are not limited to, synthetic rubber, natural rubber, polyurethane, a flexible solid polymer material referred to as sticky anti-slip gel, leather, felt made from natural and/or synthetic fibers, a polymer material cast into the preferred pad shape, a polymer material adhered to or fused to a fabric, silicone rubber, polysiloxane, emery cloth, and so on. For example, sticky anti-slip gel has a high coefficient of friction, readily adheres to many other materials, and is easily cleaned when dust or dirt adhere to the gel and impair its gripping properties. When the support sleeve 102 is worn on a leg, the friction pad 116 may be positioned over and approximately parallel to the shin bone (tibia). When an alternative embodiment of the support sleeve 102 is worn on an arm, the friction pad may be placed over and approximately parallel to the ulna.

The support sleeve may be wrapped around a limb and held in a comfortable and stable position on the limb by connecting the straps 104 to the corresponding strap connectors 108. Parts of the friction pad 116 may be compressed when the support sleeve 102 is secured to the limb. The high coefficient of friction of the friction pad's surface and compressed parts of the friction pad oppose unwanted movement of the friction pad relative to the limb, enabling embodiments of a support sleeve 102 to be held in a fixed, stable position on a limb with less strap compression and pinching than for previously known devices. The friction pad further provides a cushion for protecting the limb from externally applied forces, for example forces from applied loads and impacts. The relatively large surface area of the support sleeve 102 and the stabilizing effect of the friction pad 116 and optional collars 120 oppose movement of the support sleeve along and around the limb.

Figure 5:
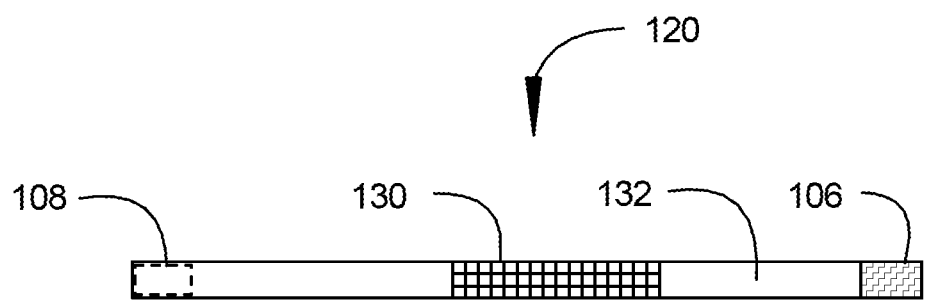
FIG. 5 shows a view toward a front side of an example of an optional collar formed as a strap having a gripping pad on a front surface of the strap.

An example of an optional collar 120 is shown in FIG. 5. The example of a collar 120 may be formed as a separate strip as suggested in the figure or may alternatively be an integral part of a sleeve. A collar 120 may further include an optional gripping pad 130 attached to, or alternately formed as an integral part of, the front surface 132 of the collar. The gripping pad 130 opposes slippage of a garment or another gripping pad in contact with the gripping pad, providing stable support for a limb guard worn over a support sleeve.

The gripping pad 130 may be made from a gripping material with a rough surface such the hook portion of thistle cloth, emery cloth, perforated metal having small protrusions extending from the surface, a substrate material with many short wires or bristles extending out from a surface of the material, the loop portion of thistle cloth, materials with magnetic properties or materials incorporating magnets, and so on. The gripping material preferably opposes slipping when pressed against skin, another piece of the gripping material, and fabric. Gripping material preferably has a high coefficient of friction compared to coefficients of friction for natural and synthetic materials commonly used for clothing. Examples of a gripping material include, but are not limited to, synthetic rubber, natural rubber, polyurethane, leather, felt made from natural and/or synthetic fibers, a polymer material cast into the preferred pad shape, a polymer material adhered to or fused to a fabric, silicone rubber, polysiloxane, emery cloth, sticky anti-slip gel, and so on.

Figure 6:
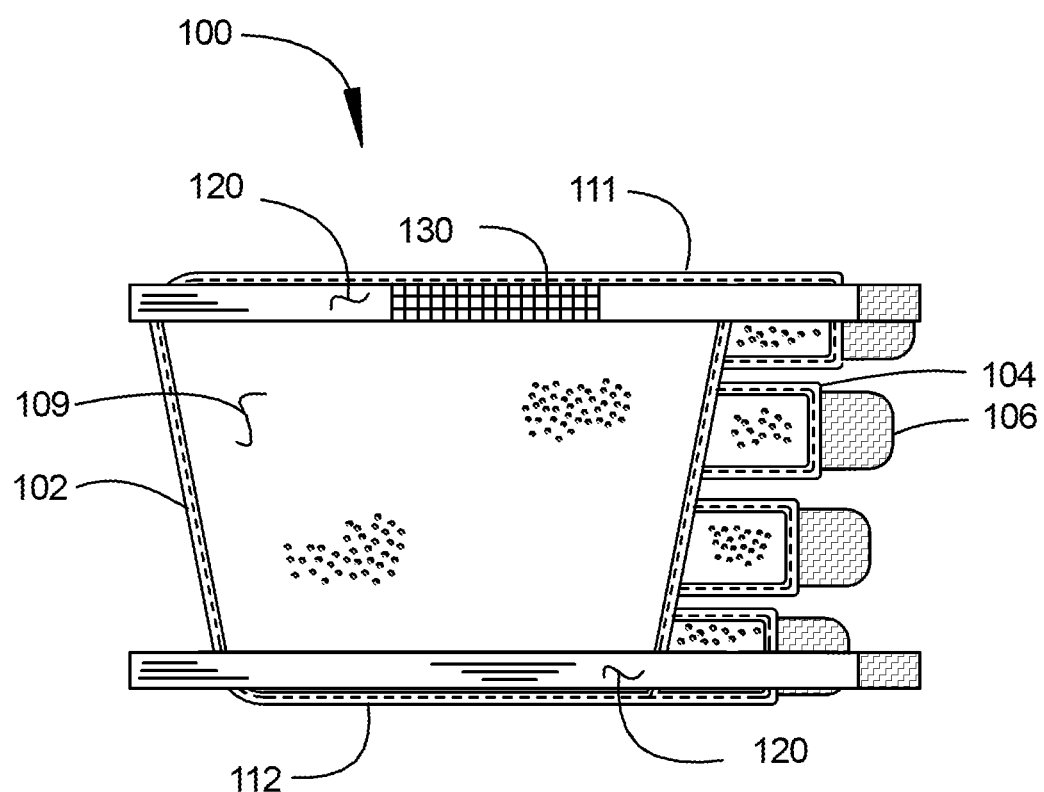
FIG. 6 shows a view toward the front side of an example support sleeve having a first optional collar coupled to a proximal transverse edge of the sleeve and a second optional collar coupled to a distal transverse edge of the sleeve.

As suggested in FIG. 6, one or more low-stretch collars 120 may optionally be attached to, or alternatively formed as an integral part of, the support sleeve 102. A first collar 120 may be positioned on the front surface 109 of the support sleeve along the proximal transverse edge 111. A second collar 120 may be positioned on the front surface of the support sleeve along the distal transverse edge 112. The collar 120 may be joined to the sleeve by fusing, stitching, adhesive, snaps, hook-and-loop fastener material, or rivets. A collar 120 joined to the support sleeve 102 may be attached to the support sleeve at one location or more than one location along the collar. Alternatively, a collar 120 may pass through one or more optional strap loops 126 as shown on the example sleeve 102 in FIG. 7. Or, one or more collars 120 may be placed around a limb separately from the support sleeve 102, in contact with the support sleeve but not attached to the support sleeve.

Figure 7:
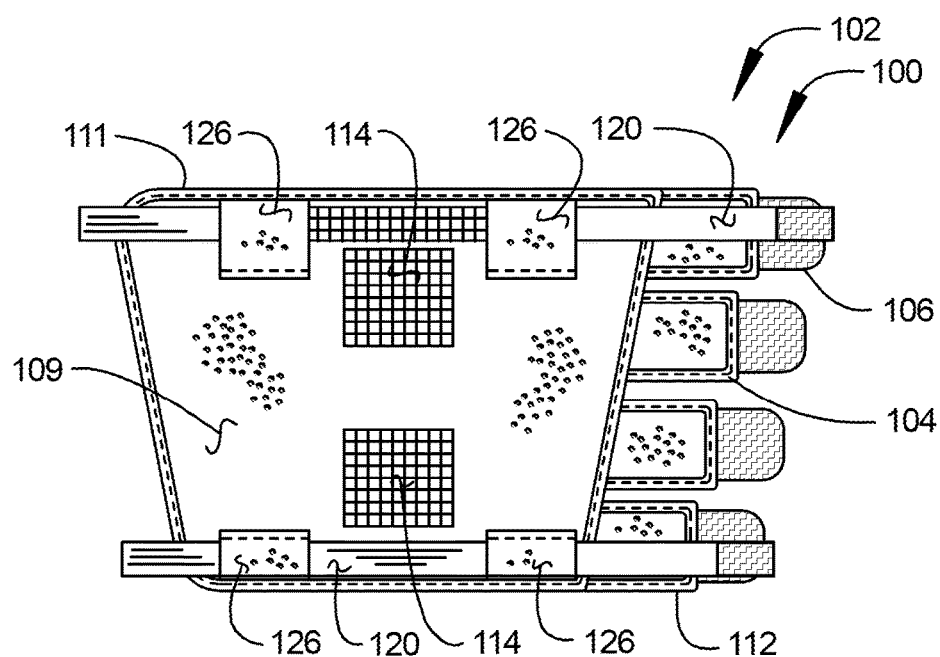
FIG. 7 shows a view toward a front surface of an example of an alternative embodiment of a support sleeve with the collar provided as a removable strap passing through strap loops on the front surface of the support sleeve.
Figure 16:
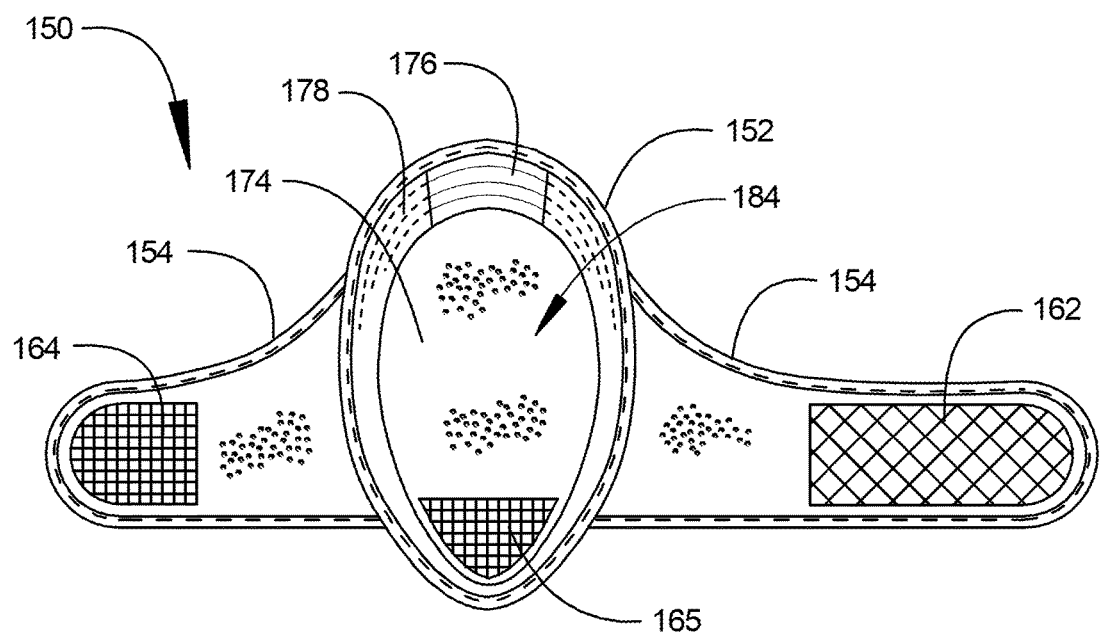
FIG. 16 shows a view toward a back side of the example of a joint guard from FIG. 15.
Figure 21:
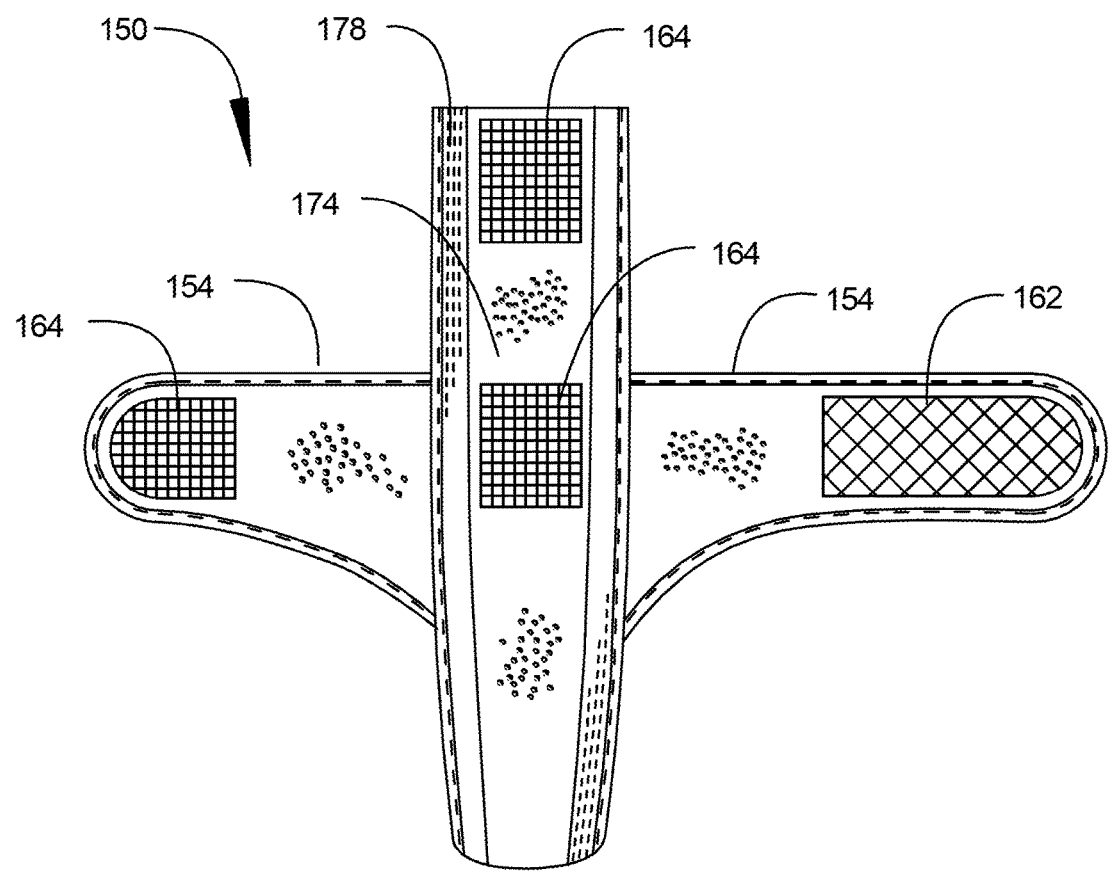
FIG. 21 shows a view toward a back side of an alternative embodiment of a limb guard having more than one gripping pad.

FIG. 7 further illustrates an example of a gripping pad 114 strongly attached to the front surface 109 of the support sleeve 102 in some embodiments 100. The gripping pad 114 on the support sleeve may be positioned for engaging with a corresponding gripping pad 165 on a limb guard 150. A gripping pad 114 positioned on the support sleeve 102 for engaging with a corresponding gripping pad 165 on a limb guard may also be referred to as a cap connector 114. An example of a gripping pad 165 positioned on a joint guard to engage with the gripping pad 114 on a support sleeve is shown in FIG. 16. An example of a gripping pad 164 positioned on a limb guard to engage with the gripping pad 114 on a support sleeve is shown in FIG. 21. The gripping pads on the support sleeve, joint guard, and/or limb guard, provide additional positional stability of the guard relative to the support sleeve, compared to a guard coupled to the sleeve by straps alone. Hook-and-loop fastener material, snaps, hooks, and other detachable fasteners, or another piece of gripping material, may be used for the gripping pad 114 and the corresponding optional gripping pad 165 on a joint guard or limb guard.

Figure 8:
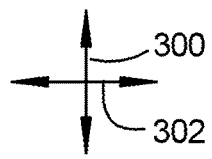
FIG. 8 shows a view toward a front side of an example support sleeve having an optional stiffener.
Figure 8:
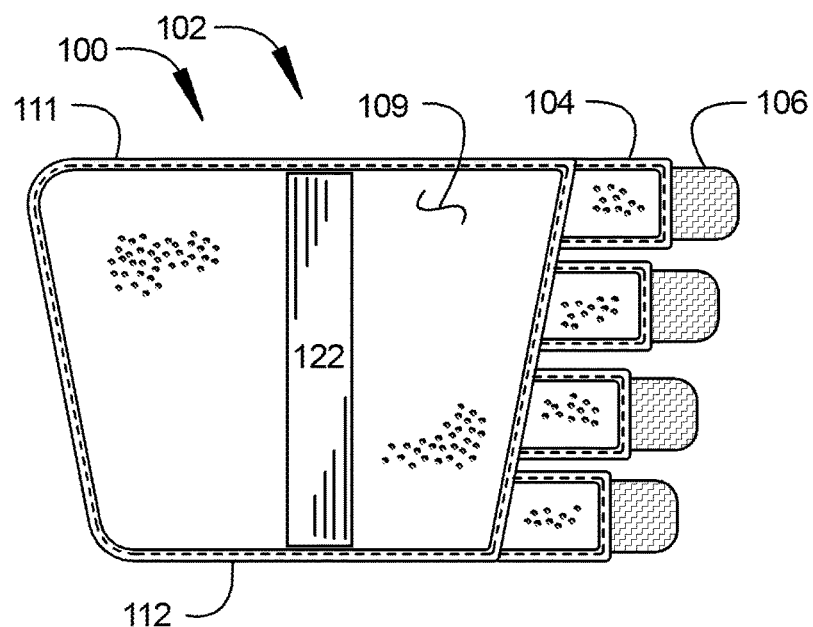

A support sleeve 102 may optionally include a stiffener to oppose stretching of the sleeve in a longitudinal direction 300 while allowing the sleeve to stretch easily in a transverse direction 302. The stiffener may further oppose longitudinal compression, wrinkling, or buckling of the sleeve. In the example of FIG. 8, a support sleeve 102 has an example of a stiffener 122 extending in a longitudinal direction 300 on the front surface 109. The stiffener may be made from nylon webbing, leather, or another material that is more resistant to stretching and buckling than the material of the support sleeve.

Figure 9:
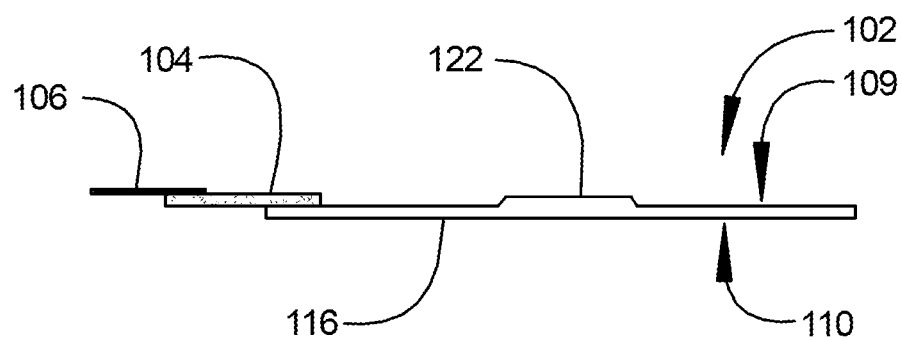
FIG. 9 is a cross-sectional view A-A of an example support sleeve having a stiffener integrally formed as a relatively thick segment of the sleeve and a friction pad forming some, or alternatively all, of the back side of the sleeve. A location and viewing direction for the cross-sectional view is marked with a section line A-A in FIG. 4.
Figure 10:
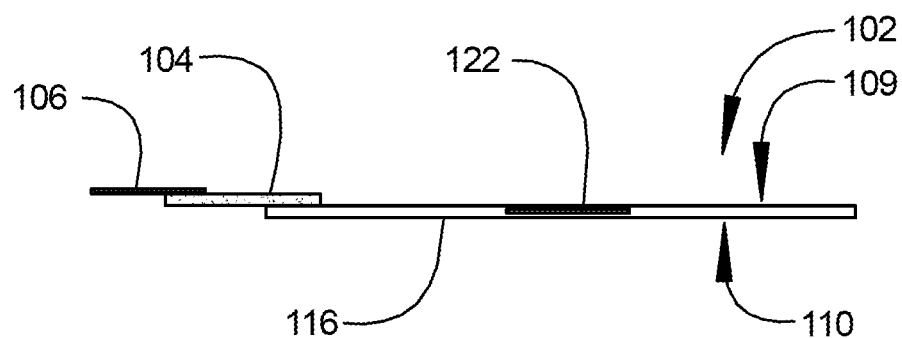
FIG. 10 is an alternative cross-sectional view A-A showing an example support sleeve having a stiffener affixed to or alternatively embedded within the sleeve, and further illustrating an example of a friction pad formed as a back surface of the sleeve.
Figure 11:
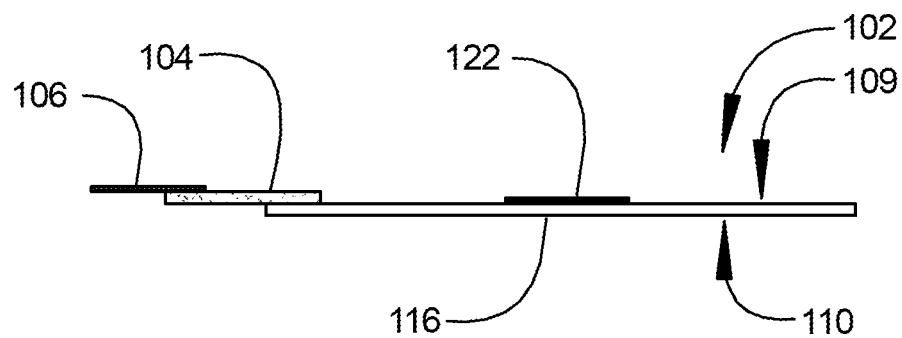
FIG. 11 is an alternative cross-sectional view A-A showing an example support sleeve having a stiffener coupled to the front side of the sleeve and a friction pad forming all, or nearly all, of the back side of the sleeve.

Alternative cross-sectional views in FIGS. 9-14 show some details of alternative embodiments of a support sleeve 102. In the example of FIG. 9, a stiffener 122 is implemented as an integral part of the support sleeve 102, with the stiffener comprising a segment with a greater thickness dimension that other parts of the support sleeve. In FIG. 10, a stiffener 122 may be embedded within the material of the support sleeve such that a surface of the stiffener is approximately coplanar with a back surface of the support sleeve. In the example support sleeve of FIG. 11, the stiffener 122 is attached to the front surface 109. FIGS. 9, 10, and 11 further illustrate an example of a support sleeve 102 where the back surface 110 is made from a material allowing the surface to function as the friction pad 116. A friction pad 116 and an optional second friction pad 118 may alternatively be formed as an integral part of the support sleeve 102.

Figure 12:
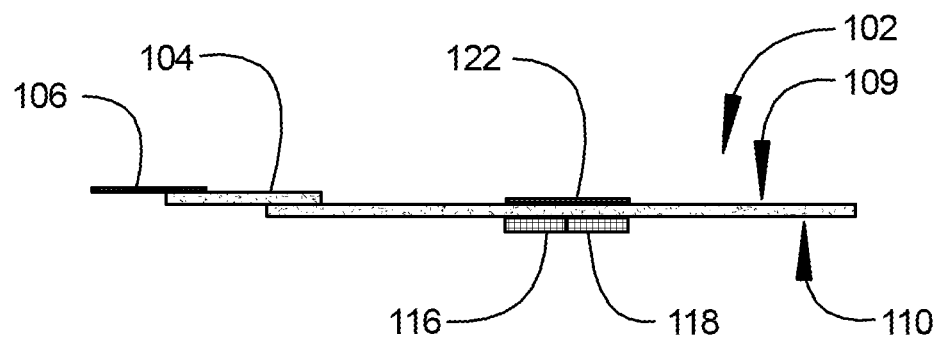
FIG. 12 is an alternative cross-sectional view A-A showing an example support sleeve having a stiffener on a front side of a sleeve, a first friction pad on a back side of the sleeve, and an optional second friction pad on the back side of the sleeve.

In the example support sleeve of FIG. 12, a stiffener 122 is attached on the front surface 109 and the friction pad 116 is attached to the back surface 110. FIG. 12 further illustrates an alternative embodiment of a support sleeve 102 having a second friction pad 118 attached to the back surface 110 adjacent the first friction pad 116.

Figure 13:
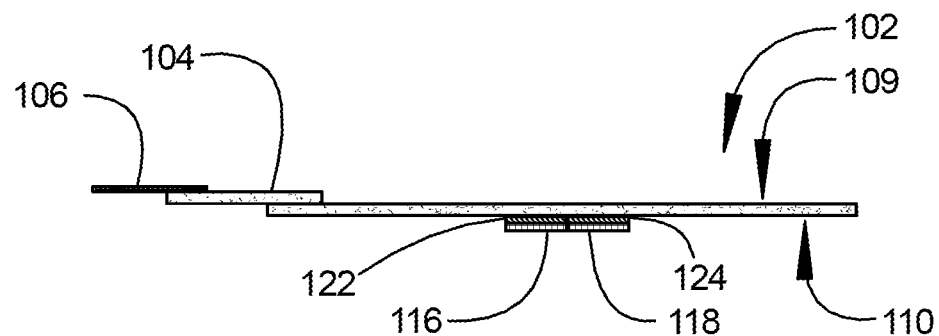
FIG. 13 is an alternative cross-sectional view A-A showing an example support sleeve having a first friction pad and an optional second friction pad on a back side of the sleeve, a first stiffener interposed between the back surface of the sleeve and the first friction pad, and a second stiffener interposed between the back surface of the sleeve and the second friction pad.

A stiffener may alternatively be interposed between the friction pad and the back surface of the support sleeve as shown in the example of FIG. 13. The example support sleeve 102 in FIG. 13 includes a first friction pad 116 and a second friction pad 118 on a back side 110 of the sleeve, a first stiffener 122 interposed between the back surface of the sleeve and the first friction pad, and a second stiffener 124 interposed between the back surface of the sleeve and the second friction pad.

Figure 14:
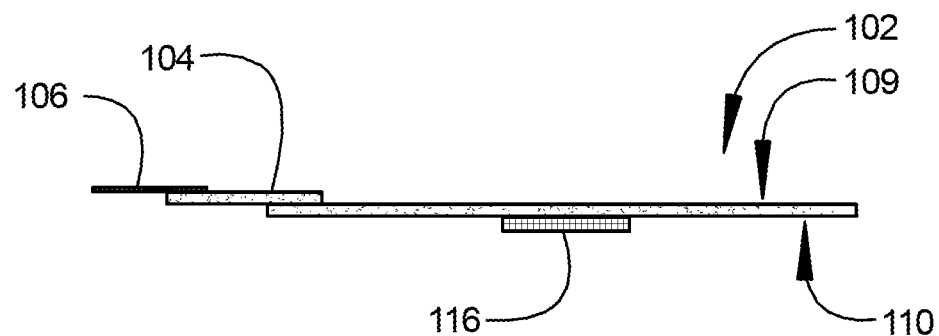
FIG. 14 is an alternative cross-sectional view A-A showing an example support sleeve having a stiff friction pad on a back surface of the sleeve.

An embodiment of a support sleeve may omit a stiffener as suggested in the example of FIG. 14. As in other example embodiments, FIG. 14 shows an example of a friction pad 116 attached to the back surface 110 of the support sleeve 102. A friction pad may optionally be configured to function as a stiffener, for example by making the friction pad with a thicker cross section than the sleeve or by making the friction pad from a material that is stiffer than the material of the sleeve.

FIGS. 15-21 show some examples of limb guards 150 suitable for use with a support sleeve 102 in an apparatus embodiment 100. Some apparatus embodiments include a limb guard 150 with the support sleeve 102. It will be appreciated that limb guards compatible with an apparatus embodiment 100 may have other shapes, sizes, and materials than are represented in the examples of the figures.

Figure 15:
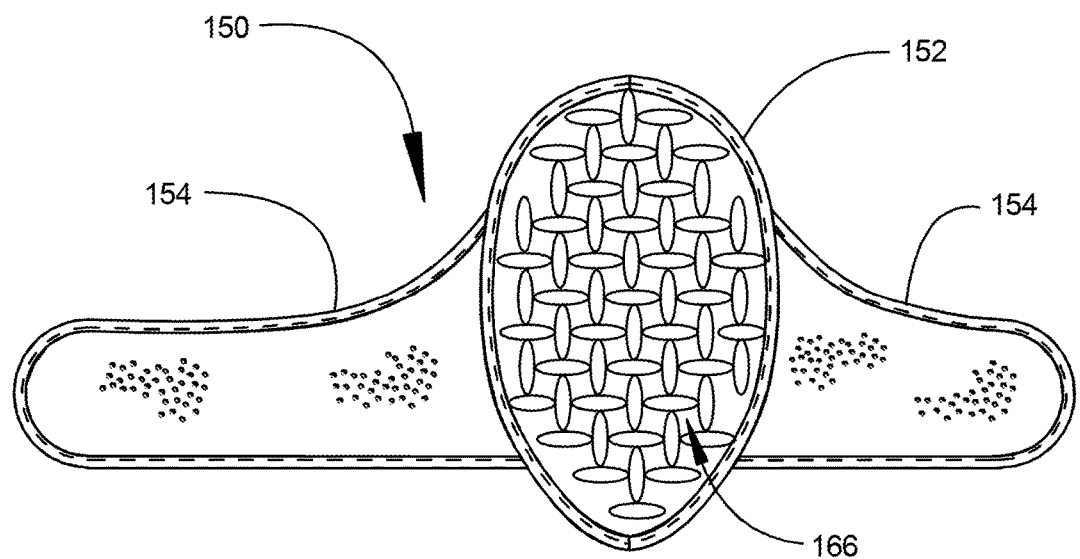
FIG. 15 shows a view toward a front side of an example of a joint guard.

FIG. 15 shows a view toward a front side of a limb guard 150 having a pair of opposing straps 154 attached to a cap 152. The opposing straps are preferably configured to connect to one another while wrapped around the support sleeve 102, as suggested in the example of FIG. 2. FIG. 16 shows a view toward the back side of the example limb guard of FIG. 15. The limb guard may include a pad 174 installed in a concave space formed on the back side 184 of the cap 152. A peripheral pad 178 may surround, or partly surround, the central pad 174. The peripheral pad 178 may optionally include a section 176 that is softer, i.e. more easily compressed, than the peripheral pad 178. The softer section 176 provides a comfortable contact area for parts of the limb pressing against the limb guard when the limb is in its extended or straightened position.

An optional gripping pad 164 may be positioned on the back surface 184 of the limb guard 150, for example on a strap 154, to stabilize the limb guard 150 against a limb and sleeve 102. The cap 152 may optionally be detachable from other parts of the limb guard 150. A strap connector 162 is provided for connecting the two straps 154 to one another. The gripping pads (164,165) may function as a connector for attaching the limb guard to the sleeve or to another limb guard.

Figure 17:
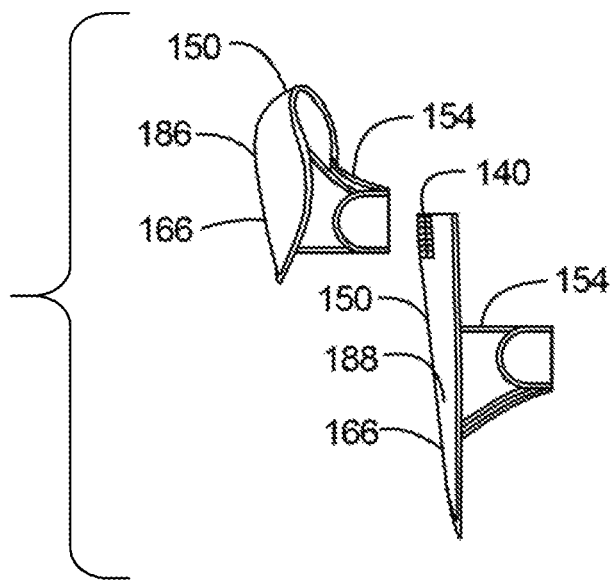
FIG. 17 is a side view of an example of an alternative embodiment of an apparatus having a two-part limb guard configured to cover a joint and a segment of a limb.
Figure 18:
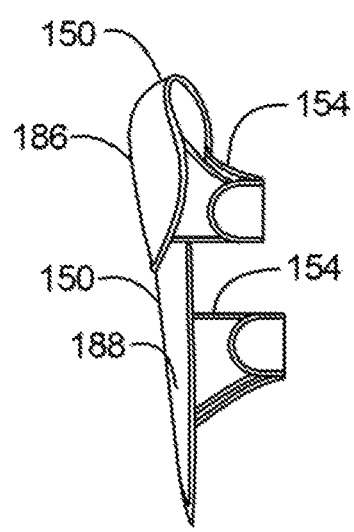
FIG. 18 shows another side view of the example limb guard of FIG. 17, with the two parts of the limb guard in contact with one another for protecting a person's knee joint and shin.
Figure 19:
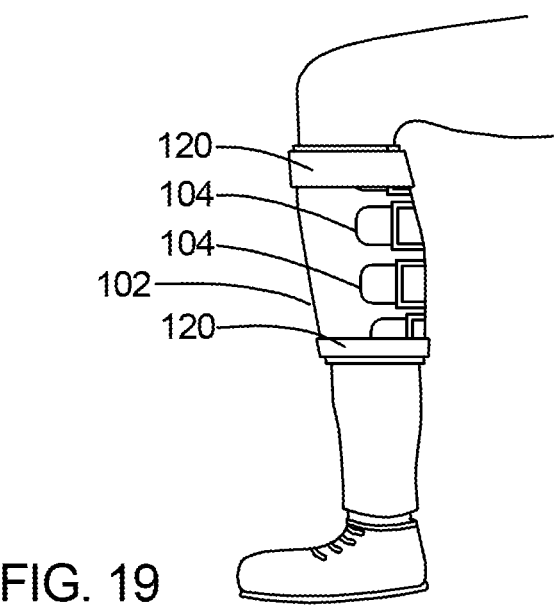
FIG. 19 shows a side view of an example of a support sleeve suitable for use with any of the limb guard examples disclosed herein.
Figure 20:
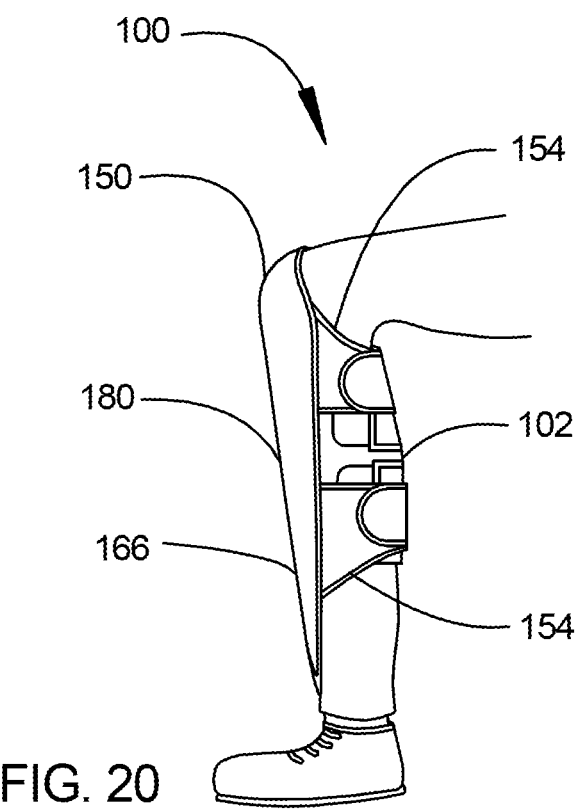
FIG. 20 shows a side view of an alternative embodiment of a limb guard having a joint guard and a shin guard formed into a unitary structure.

FIG. 17 shows an example of a limb guard 150 configured as a knee guard 186 and further configured to be worn with a shin guard 188. The shin guard 188 may contain a gripping pad 140 positioned on a front surface 166 to contact the gripping pad 165 on the back surface 184 of the limb guard 150. FIG. 18 shows a side view of the knee guard 186 positioned over the shin guard 188 such that the straps 154 on both limb guards 150 will wrap over the example of a support sleeve 102 in FIG. 19, as suggested in FIG. 20. As with other apparatus embodiments 100, all of the straps 104 of the support sleeve 102 are preferably worn on a same side of a joint on the limb being protected. The strap 154 on the example knee guard 186 and the strap 154 on the example shin guard 188 are configured to wrap over and around the support sleeve 102, with the support sleeve interposed between the limb guards 150 and the limb. FIG. 20 further shows an example of a limb guard 150 with a knee guard and a shin guard formed as a single integrated unit 180. As with the other example embodiments disclosed herein, the support sleeve may be worn under a garment and the limb guard may be worn over the garment.

FIG. 21 shows an example of a limb guard having more than one gripping pad 164 positioned for stabilizing the limb guard against a limb. A gripping pad 164 may optionally be positioned to contact a corresponding gripping pad 114 on a support sleeve.

Any of the gripping pads (e.g. 164, 165), cap connector (e.g., 114), and/or friction pads (e.g., 116, 118) disclosed herein may be made from a gripping material, or alternatively more than one of the gripping materials. In some embodiments, a gripping pad and a friction pad may be made from a same material. All gripping pads in an embodiment of a support sleeve and/or limb guard may not be made from a same gripping material. In alternative embodiments, a gripping pad and a friction pad may be made from different materials. Gripping pads positioned on different parts of an embodiment of a support sleeve and/or a limb protector may optionally be made from different materials.

In some embodiments, an optional strap may extend from the proximal end of a limb guard or a joint guard worn over the support sleeve. The optional strap may wrap around the limb on a side of the joint opposite the side with the support sleeve to prevent the limb guard from falling away from the joint when the person moves about. The optional strap, if present, is not required to prevent the support sleeve or joint guard from slipping along the limb or rotating about the limb.

An embodiment of a limb guard may optionally be provided separately from an embodiment of a support sleeve. The limb guard preferably includes at least two straps attached to the limb guard, the straps positioned to connect to one another and to wrap around a support sleeve. The limb guard may further include a gripping pad attached to a back side of the limb guard, the gripping pad positioned to contact a gripping pad on the support sleeve.

Unless expressly stated otherwise herein, ordinary terms have their corresponding ordinary meanings within the respective contexts of their presentations, and ordinary terms of art have their corresponding regular meanings.

What is claimed is:

1. An apparatus, comprising:
a support sleeve formed from an elastic material, comprising:
a front surface, comprising:
a proximal transverse edge;
a distal transverse edge opposite said proximal transverse edge;
a first side extending from said proximal transverse edge to said distal transverse edge; and
a second side transversely opposite said first side, said second side extending from said proximal transverse edge to said distal transverse edge;
a back surface;
a first elastic strap extending transversely outward from and affixed to said first side, said first elastic strap comprising a first strap connector;
a second elastic strap extending transversely outward from and affixed to said first side, said second elastic strap comprising a second strap connector;
a third strap connector attached to said front surface, said third strap connector positioned adjacent said second side and extending from said proximal transverse edge to said distal transverse edge, said third strap connector attachable to said first and second strap connectors; and
a friction pad attached to said back surface;
a first collar formed as a strap, said first collar attached to said front surface of said support sleeve along said proximal transverse edge, said first collar comprising a first end extending transversely outward from said first side of said front surface, a second end extending transversely outward from said second side of said front surface, and said first end of said first collar connectable to said second end of said first collar;

a second collar formed as a strap, said second collar attached to said front surface of said support sleeve along said distal transverse edge, said second collar comprising a first end extending transversely outward from said first side of said front surface, a second end extending transversely outward from said second side of said front surface, and said first end of said second collar connectable to said second end of said second collar;

wherein said first collar, said second collar, and said friction pad on said support sleeve have lower stretch than other parts of said support sleeve, and all of said elastic straps on said support sleeve are configured to be wrapped around a same side of a limb joint.

2. The apparatus of claim 1, wherein said first collar further comprises a front surface and a gripping patch positioned on said front surface of said first collar.

3. The apparatus of claim 1, further comprising a strap loop positioned on said front surface of said support sleeve to hold said first collar.

4. The apparatus of claim 3, further comprising a second strap loop positioned on said front surface of said support sleeve to hold said second collar.

5. The apparatus of claim 1, wherein said friction pad extends from said proximal transverse edge to said distal transverse edge.

6. The apparatus of claim 1, further comprising a limb guard comprising:

a limb guard back surface configured for contact with said support sleeve; and two opposing straps configured to connect to one another and to wrap around said front surface of said support sleeve, said limb guard removable from said support sleeve by disconnecting said two opposing straps from one another.

7. The apparatus of claim 6, said limb guard further comprising:

a compressible pad;

a cap attached to said compressible pad;

a gripping pad attached to said limb guard; and a gripping pad attached to said support sleeve, said gripping pad on said support sleeve positioned for contact with said gripping pad on said limb guard, wherein all of said opposing straps on said limb guard are configured to be wrapped around said support sleeve on a same side of the limb joint.

8. The apparatus of claim 7, wherein said cap is configured for removable attachment to said limb guard.

9. The apparatus of claim 1, wherein said support sleeve further comprises a stiffener extending longitudinally along said support sleeve.

10. The apparatus of claim 9, wherein said stiffener is attached to said front surface of said support sleeve.

11. The apparatus of claim 9, wherein said stiffener is interposed between said back surface of said support sleeve and said friction pad.

12. The apparatus of claim 1, further comprising a knee guard and a shin guard formed as an integrated unit, said integrated unit including a pair of opposing straps configured to wrap around said support sleeve, wherein all of said straps on said integrated unit are configured to wrap around a same side of the limb joint.

* * * * *